United States Patent [19]

Keith et al.

[11] Patent Number: 4,862,505
[45] Date of Patent: Aug. 29, 1989

[54] AUDIOMETER WITH INTERACTIVE GRAPHIC DISPLAY FOR CHILDREN

[76] Inventors: William J. Keith, 16 Paris Place, Birkenhead, Auckland; Michael Parsons, 6 Hurunui Street, Cashmere, Christchurch; Russell P. Smith, 14 View Terrace, Huntsbury, Christchurch; Christopher J. Glenn, 5 Titoki Street, Fendalton, Christchurch; Stephen Bell, 131 Major Hornbrook Rd., Mt. Pleasant, Christchurch, all of New Zealand

[21] Appl. No.: 113,220

[22] Filed: Oct. 23, 1987

[30] Foreign Application Priority Data

Oct. 23, 1986 [NZ] New Zealand ............ 218051

[51] Int. Cl.⁴ .......................... H04R 29/00
[52] U.S. Cl. ........................ 381/60; 73/585
[58] Field of Search .......... 84/470 R, 478; 381/68.2, 60; 73/585; 128/746

[56] References Cited

U.S. PATENT DOCUMENTS 4,321,853 3/1982 Tumblin .................. 84/470 R

FOREIGN PATENT DOCUMENTS 2354746 1/1978 France .
WO85/00509 2/1985 PCT Int'l Appl. .
2030753 4/1980 United Kingdom .

OTHER PUBLICATIONS

"Listen User's Guide", (Manual for Listen Software, by Resonate, Menlo Park, California), (first advertised & placed on sale to the public in Mar. 1986).

Primary Examiner—Forester W. Isen
Attorney, Agent, or Firm—Merchant, Gould, Smith, Edell, Welter & Schmidt

[57] ABSTRACT

A microprocessor-based audiometer for use with children. A color visual display unit is used to display an image digitally stored in memory or on disk drive to attract the childs attention and hold its concentration during testing.

The child activates a response switch upon detecting the tones produced by audiometer to the generator. Correct responses are reinforced by progressive alteration of the displayed image to increasingly desirable states.

3 Claims, 1 Drawing Sheet

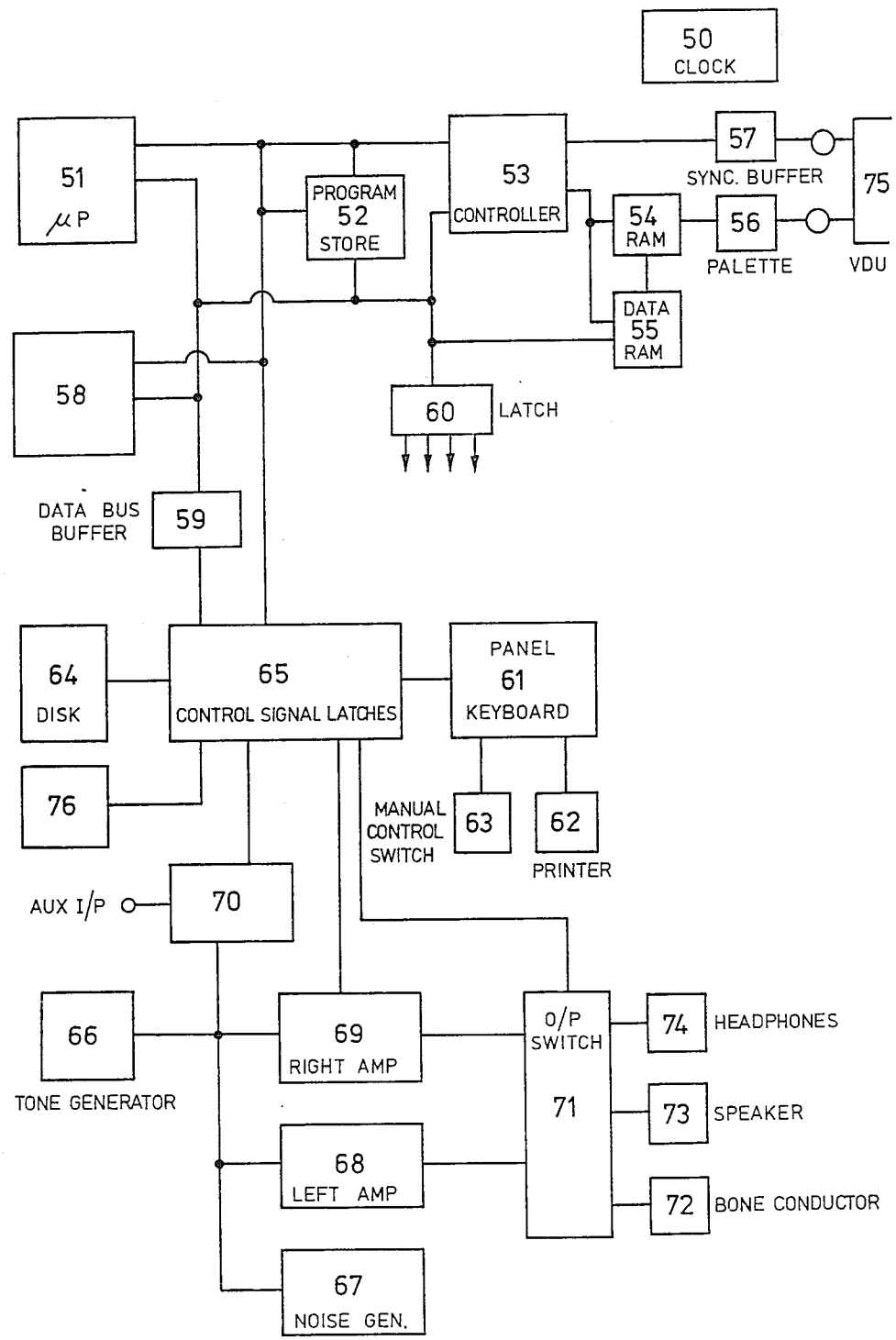

AUDIOMETER WITH INTERACTIVE GRAPHIC DISPLAY FOR CHILDREN

FIELD OF INVENTION

The invention relates to audiometers and in particular to an audiometer for use with children between the ages of 3 and 7. The audiometer may be used for both screening children for audiological referral and for testing.

PRIOR ART

It is difficult to properly test the hearing of young children using conventional audiometers due to the limited concentration span of children of such ages. A considerable amount of psychology must be practiced by the audiologists and a parent of the child to achieve results.

One device used to address the above difficulties takes the form of a mechanical puppet. The puppet may be made to move and/or make a noise as a result of a correct response from the child being tested. An example is a mechanically actuated "dog" contained within a clear plastic case. A variation of this technique is a doll placed within a smoked perspex cabinet which is rendered visible only when an internal light is switched on. All of these devices are limited to one "picture" per device which has only two states—off or on.

SUMMARY OF THE INVENTION

It is an object of the present invention to provide an audiometer which provides infinitely changeable visual reinforcement of favourable responses from the child to detected tones.

The audiometer of the present invention includes as the basic testing components: a frequency and level programmable tone generator, an electric-acoustic transducer driven by the tone generator to supply sound to the child whose hearing is being tested, and a response device operated by the child in response to detected acoustic tones. A microprocessor is interfaced to the response device and tone generator. A video display unit for viewing by the child being tested is supplied with video signals from a graphics controller in response from commands from the microprocessor. Data representative of one or more graphics sequences is stored in a memory device which is accessed by the controller. The graphics sequence is alterable to a more favourable sequence upon command from the microprocessor. The microprocessor is programmed to cause a first graphics sequence to be displayed, to cause the tone generator to produce predetermined frequencies at predetermined levels for brief periods. The program causes the microprocessor to issue an alter command to the graphics controller upon detecting a change of state of the response device within a time window subsequent in time to each tone period.

BRIEF DESCRIPTION OF THE DRAWING

The drawing shows a block circuit diagram of the present audiometer.

DETAILED DESCRIPTION OF THE PREFERRED EMBODIMENT

The purpose of an audiometer is to measure the threshold of hearing at various frequencies, usually in the range from 500 Hz to 4K Hz. At each frequency a tone is produced, usually in a headphone worn by the patient and the level of the tone is reduced in steps until it is no longer heard then increased until it is heard again. Several such threshold crossings may be used to accurately establish the threshold. The patient indicates detection of the tone by operating a switch device. The results of such testing are conventionally recorded as an "audiogram" or a plot of hearing threshold for each ear at the test frequencies.

With young children as patients it is extremely difficult to attract their attention and interest in such test with the result that they may not concentrate properly and reliably respond to the test tones as each is heard during the full time required for a test sequence. The present invention uses a colour video display unit (CRT) showing a microprocessor produced image to both attract the child's attention and to provide positive reinforcement to legitimate responses by the child during testing. For reinforcement purposes the graphics sequence is alterable in a manner favourable to the child upon activation of the switch device within a preset time window following initiation of each tone. For example, a "moving" train may be displayed with children or faces displayed in an offset region of the display unit. This constitutes the "attract" mode. At the start of testing the trains stops at a station and the image changes to a carriage with windows. A positive response from the child to a tone will cause a face to be moved into a train carriage and appear at a window. Further positive response will progressively move faces into the carriage. Other graphic sequences have been found equally satisfactory for this purpose. They all essentially involve the realisation of a goal which the child finds desirable. Examples of alternative image themes include a bus, a boat, an airplane and a teddy bear who dresses step by step.

The audiometer may be used as both a screening tool and for complete audiological testing. In the former mode tone generation and level adjustment will be controlled by a prestored program. In the screening mode hearing is checked at preset levels at the four main frequencies at each ear. The test runs automatically under the control of the audiometer program. If there is no response at a screening level at a particular frequency it is checked again starting at a higher intensity. In any of the modes where automatic testing is selected the response time window is adapted to match the speed of response from the child. Similarly the intervals between each test tone are adaptively controlled. In the test mode a manual option may be selected if desired.

Three operating modes have already been mentioned. A fourth mode is a "practice" mode. This is used to condition a child prior to conducting an actual test. The child is encouraged to activate the response switch to produce the tones which would be heard during testing in a loud speaker unit. Conditioning therefore can be started by using the sound field tone before changing to the headphones required for testing. Activation alters the picture shown on the display unit.

Referring to the drawing the microprocessor based audiometer is essentially self-contained in a console except for the video display unit 75 and response switch 76. A hearing test is started when an appropriate key is pressed on the console panel display and keyboard 61. A non-volatile program memory 52 preferably also stores graphics data and microprocessor 51 writes data corresponding to a picture (e.g. the train carriage) into video RAM 54. Video system controller 53 fetches this data from video RAM 54 and displays it on the video display unit 75. The data is processed by colour palette 56 to increase the attractiveness of the displayed colours. Synchronisation signals for the display unit 75 are provided by video system controller 53 and buffered by synchronisation signal buffer 57.

To determine if the subject can hear a tone at a given frequency and audio level, microprocessor 51 outputs suitable control signals through control signal latches 65 causing tone generation circuitry 66 to generate a tone at a certain frequency. Either left channel amplifier 68 or right channel amplifier 69 amplify the tone to a selected level. Output switching circuitry 71 directs the tone to either bone conductor 72, free field speaker 73 or headphones 74. Control signal latches 65 may also direct the output of auxiliary input selection 70 or noise generation circuit 67 to left channel amplifier 68 or right channel amplifier 69.

The tone is presented to the subject for a predetermined length of time. If the subject presses the response switch 76 within a predetermined time from the start of the tone presentation, the microprocessor 51 records a positive response in the data RAM 55 and rewrites data in video RAM 54, thereby changing the picture displayed on display unit 75 in a manner which is considered more favourable by the subject being tested. This has been described above.

In the event that the response switch 76 is not activated within a predetermined time of the tone being presented, no change is made to the data in video RAM 54 and hence there is no change to the picture displayed on display unit 75. This is perceived as a less favourable situation by the subject being tested.

In the event of a positive response being obtained to a presentation at a given frequency and level, the level of the tone is decreased and another test performed. In the event that a negative response to the tone is obtained, the level is increased and the test repeated. The form of such tests used are those which are well known in the art.

The results of the hearing test may be displayed on front panel display and keyboard 61 and may optionally be printed on a thermal printer 62 or stored on floppy disk drive with controller 64.

The picture data for display unit 75 may be stored in program memory 52 or on a floppy disk in drive 64. This data may be generated by well known "paint" type software available for personal computers. It is coded and compressed to a form suitable for use in this audiometer. The picture data corresponds to one or more background pictures and a variety of images (e.g. faces) which on command may be superimposed on the background picture. The picture data includes codes indicative of pixel colour and these raw colours are enhanced by the use of the palette 56 which typically enables a selection from 4096 stored colours.

Conventional manual operation of the audiometer is available by operation of keys on the front panel display and keyboard 61 and the rotary switch 63.

In order to obtain the subject's attention before the start of a hearing test, microprocessor 51 can move data in video RAM 54 to provide a moving display on colour monitor 75. This is the "attract" mode previously described.

The present invention has equal applicability to audiometers capable of simple screening tests and to audiometers capable of full clinical testing. The form of tests used are those which are well known in the art but with the present invention, screening and threshold tests of both ears can be performed on young children without the intervention of a skilled audiologist. The range of available scenes and their ease of modification enable testing of young children with an extremely short attention span who would become quickly bored with a single scene or testing environment.

What is claimed is:

1. An audiometer for use with young children comprising:
   (a) a frequency and level programmable tone generator;
   (b) an electric-acoustic transducer driven by said tone generator to supply sound to the child whose hearing is being tested;
   (c) a two-state response switch operated by the child in response to detected acoustic tones;
   (d) a microprocessor having input-output ports to which the response switch and tone generator are connected;
   (e) a video display unit for viewing by the child;
   (f) a graphics controller which drives said display unit connected to a further input-output port of said microprocessor;
   said microprocessor being programmed to cause a first picture sequence to be displayed, to activate said tone generator at predetermined frequencies and levels, including levels deliberately inaudible to the child, and to alter the first picture sequence to a more favorable picture sequence upon detecting a change of state of the response device within a time window subsequent in time to each tone period.

2. A method for testing hearing in a patient comprising:
   (a) producing an attract mode graphics display visually perceptible to the patient;
   (b) producing a plurality of tones of predetermined frequencies and amplitudes, at least one of said tones having an amplitude which is deliberately inaudible to the patient;
   (c) supplying the tone produced to the patient;
   (d) providing the patient with means for indicating whether the patient perceived the tone within a predetermined time period;
   (e) determining whether the patient indicated that the patient perceived the tone within the time period; and
   (f) changing the graphics display if it is determined that the patient responded to the tone within the time period.

3. A method for testing hearing in young children comprising:
   (a) programming a microprocessor to generate picture sequences for video display to the child;
   (b) generating a first picture sequence to be visually displayed to the child;
   (c) programming a microprocessor to generate control signals for generating tones of a frequency and level selected from a range of frequencies and levels which includes frequencies and levels which correspond to tones which are inaudible to the child;
   (d) generating a tone at an electric-acoustic transducer controlled by the control signals generated by the programmed microprocessor;
   (e) supplying the generated tone to the child whose hearing is to be tested;

(f) providing the child with a two-state response switch which produces a response signal when operated by the child in response to the generated tone;

(g) inputting the response signal from the two-state response switch into the microprocessor; and (h) generating a second picture sequence when a response signal is inputted into the microprocessor within a predetermined response time following the generating of a tone.

* * * * *